June 22, 1954 E. S BOERNER Plant Pat. 1,286
ROSE PLANT
Filed June 2, 1953
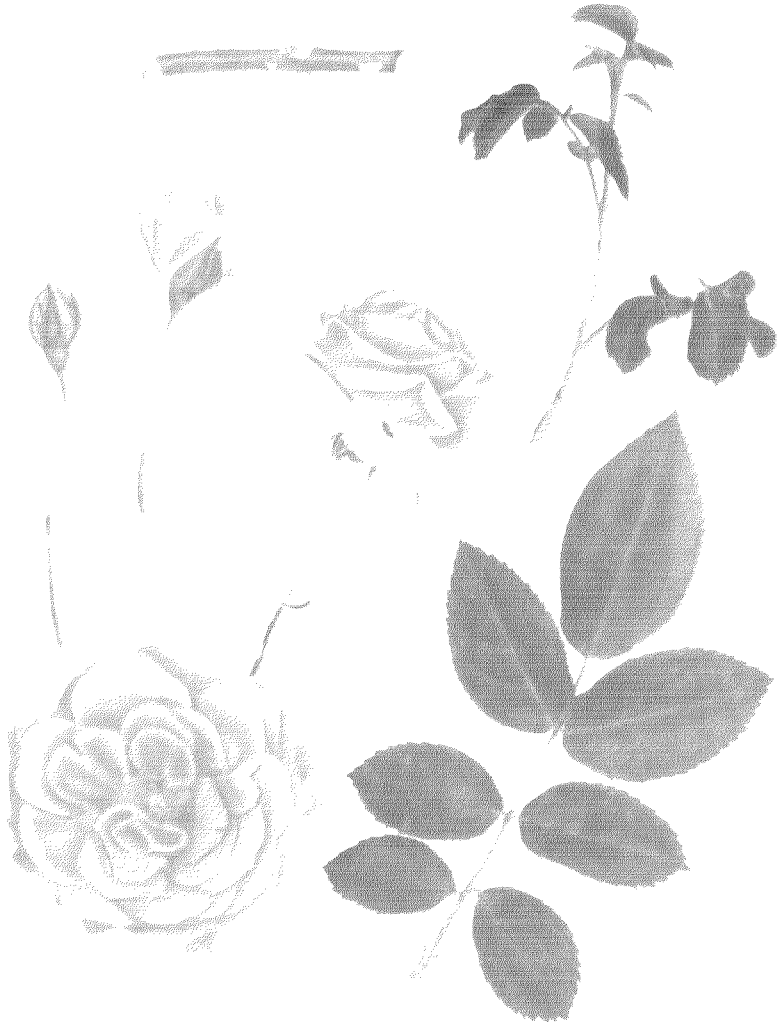
Inventor.
E. S. Boerner
By: Robb & Robb
Attorneys.

Patented June 22, 1954 Plant Pat. 1,286

UNITED STATES PATENT OFFICE 1,286

ROSE PLANT

Eugene S. Boerner, Newark, N. Y., assignor to Jackson & Perkins Company, Newark, N. Y., a corporation of New York Application June 2, 1953, Serial No. 359,243

1 Claim. (Cl. 47—61)

The present invention relates to a new and distinct variety of rose plant of the large-flowered polyantha class, which was originated by me by crossing an unnamed and unpatented peach-colored seedling of the variety "Pinocchio" (Plant Patent No. 484) with the variety "Fashion" (Plant Patent No. 789).

The primary objective of this breeding was to produce a new rose variety of the "Pinocchio" type so far as the general plant habits are concerned, while at the same time, combining therewith the flower color and hardiness characteristics that are typical of the variety "Fashion." This objective was fully achieved, as evidenced by the following characteristics which are outstanding in my new variety, and which distinguish it from its parents, as well as from all other varieties of its class:

(1) The typical cupped shape of "Pinocchio" type flowers;

(2) Increased petalage of the flowers, averaging from 65 to 70 petals;

(3) A unique and distinctive color in the half-open flower, which may be specifically described as Geranium Pink with a suffusion of Light Cadmium in the lower half of the petals;

(4) The typical "Pinocchio" type of plant, with the characteristic Yellowish Oil Green overcast with Oxblood Red coloring of the young foliage of the variety "Fashion";

(5) The oval-pointed leaflets comparable to those of "Fashion," but combined with the compact and other general overall growing habits of "Pinocchio"; and (6) A hardiness comparable to that of "Fashion."

Asexual reproduction of my new variety by budding at Newark, New York, and at Pleasanton, California, shows that the foregoing characteristics and distinctions come true to form and are established and transmitted through succeeding propagations.

The accompanying drawing shows typical specimens of the flowers, foliage and stems of my new variety in different stages of development, and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—An unnamed peach-colored seedling of "Pinocchio."

*Pollen parent.*—"Fashion."

Classification:

*Botanic.*—Large-flowered polyantha;

*Commercial.*—Floribunda.

*Flower*

(Observations made in a greenhouse at Newark, New York, in the early morning in the early part of the month of May.)

Blooming habit: Recurrent—continuous.

Bud:

*Size.*—Medium.

*Form.*—Ovoid; is not affected by wet or hot weather.

*Color.*—When sepals first divide—Begonia Rose, Plate 1. When petals begin to unfurl—Eosine Pink, Plate 1. When half blown: inside of petals—La France Pink, Plate 1, lightly overcast with Eosine Pink, Plate 1; reverse of petals—Geranium Pink, Plate 1, with suffusion of Light Cadmium, Plate 4 in the lower half of the petals.

*Sepals.*—Branched; curl back when petals begin to unfurl. Color: inside—Light Lumiere Green, Plate 17; outside—Light Bice Green, Plate 17.

*Calyx.*—Color — Lettuce Green, Plate 5. Shape — pear. Size — small. Aspect—smooth. Odor when rubbed—none.

*Peduncle.*—Length—short. Aspect—smooth. Strength—erect; slender. Color—Lettuce Green, Plate 5.

*Opening.*—Opens well; is not affected by adverse weather conditions.

Bloom:

*Size.*—Medium; average size when fully expanded—2½ inches.

*Borne.*—Several together and in irregular clusters.

*Stems.*—Medium length; normal strength.

*Form (when first open).*—Cupped. Permanence—retains its form to the end, but outer petals curl back.

*Petalage.*—Very double. Number of petals under normal conditions—65 to 70.

*Color.*—Center of flower—Eosine Pink, Plate 1, with suffusion of Capucine Yellow, Plate 3 in the lower half of the petals. Outer petals—La France Pink, Plate 1, lightly overcast with Geranium Pink, Plate 1, with suffusion of Buff Yellow, Plate 4 in the lower half of the petals. Base of petals (aiglet)—Pale Greenish Yellow, Plate 5. Inside of petals—Eosine Pink, Plate 1, lightly overcast with La France Pink, Plate 1. Reverse of petals—La France Pink, Plate 1, with suffusion of Safrano Pink, Plate 2 in the upper half of the petals and a suffusion of Apricot Yellow, Plate 4, in the lower half of the petals. General tonality from a distance—Eosine Pink, Plate 1.

*Discoloration.*—General tonality at end of first day—Eosine Pink, Plate 1. Second day—Eosine Pink, Plate 1, overcast with La France Pink, Plate 1. Third day—La France Pink, Plate 1, lightly overcast with Eosine Pink, Plate 1.

Petals:

*Texture.*—Thick; is not affected by wet or hot weather.

*Appearance.* — Inside — satiny. Outside—shiny.

*Form.*—Oval.

*Arrangement.*—Informal (with "rags" in center).

*Petaloids in center.*—Few; small.

*Persistence.*—Drop off cleanly.

*Fragrance.*—Moderate. Nature—tea (average hybrid tea scent).

*Lasting quality.*—On the plant—long. As cut flower—long.

*Genital organs*

Stamens, anthers: Small; few.

*Arrangement.*—Mixed with petaloids.

*Color.*—Cadmium Orange, Plate 3.

Stamens, filaments (threads): Medium length. Color—Martius Yellow, Plate 4.

Pollen: Color—Maize Yellow, Plate 4.

Styles: Bunched; uneven length; medium length; thin.

Stigmas: Color—Citron Yellow, Plate 16.

Ovaries: All enclosed in calyx.

Hips: None.

Seeds: None.

*Plant*

Form: Bush.

Growth: Vigorous; compact.

Foliage: 5 to 7 leaflets.

*Size.*—Medium.

*Quantity.*—Abundant.

*Color.*—New foliage: upper side—Yellowish Oil Green, Plate 5, overcast with Oxblood Red, Plate 1; under side—Oil Green, Plate 5, overcast with Oxblood Red, Plate 1. Old foliage: upper side—Forest Green, Plate 17; under side—Bice Green, Plate 17.

*Shape.*—Oval-pointed.

*Texture.*—upper side—smooth. Under side—smooth.

*Ribs and veins.*—Prominent.

*Edge.*—Serrated (saw-toothed).

*Serration.*—Single; sharp.

*Leaf stem.*—Color—Absinthe Green, Plate 31. Under side—prickles.

*Stipules.*—Medium length; smooth.

Wood:

*New wood.*—Color—Parrot Green, Plate 6. Bark—smooth.

*Old wood.*—Color—Bice Green, Plate 17. Bark—smooth.

Thorns:

*Thorns.*—Quantity: on main stalks from base—ordinary; on laterals from stalk—ordinary. Form — flat base; medium length; hooked downward. Position—irregular. Color (when young)—Alizarine Pink, Plate 13.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by its compact growing habit and other general overall plant characteristics similar to those of the variety "Pinocchio" (Plant Patent No. 484), by its hardiness which is comparable to that of the variety "Fashion" (Plant Patent No. 789), by its oval-pointed leaflets comparable to those of the aforesaid "Fashion" variety, by the cupped shape of its flowers comparable to those of the aforesaid variety "Pinocchio," by the very double petalage of its flowers, by the distinctive coloring of its flowers especially in the half-open stage, and by the distinctive coloring of its young foliage comparable to that of "Fashion."

No references cited.